United States Patent [19]

Sullenger

[11] Patent Number: 4,892,091
[45] Date of Patent: Jan. 9, 1990

[54] SCRATCHING DEVICE

[76] Inventor: Don R. Sullenger, 15721 Blaine #B, Bellflower, Calif. 90706

[21] Appl. No.: 249,328

[22] Filed: Sep. 26, 1988

[51] Int. Cl.$^4$ .............................................. A61H 7/00
[52] U.S. Cl. .................................... 128/62 R; 128/67
[58] Field of Search .................. 128/63, 67, 368, 365, 128/58, 62 R; 15/222

[56] References Cited

U.S. PATENT DOCUMENTS

| | | | |
|---|---|---|---|
| 1,058,273 | 4/1913 | Thompson | 128/67 |
| 1,367,747 | 2/1921 | Keplinger | 15/222 |
| 1,379,925 | 5/1921 | Kawasaki | 15/222 |
| 1,382,436 | 6/1921 | Malm | 128/62 R |
| 2,154,831 | 4/1939 | Booharin | 15/222 |
| 2,238,967 | 4/1941 | Brown | 15/222 |
| 2,807,815 | 10/1957 | Maek | 128/63 |
| 2,905,957 | 9/1959 | Volpe | 15/222 |
| 4,091,491 | 5/1978 | Hoffman | |
| 4,168,704 | 9/1979 | Wessel | 15/222 |
| 4,249,521 | 2/1981 | Gueret | |
| 4,336,623 | 6/1982 | Lin | 15/222 |
| 4,667,659 | 5/1987 | Hayday | 128/62 R |

Primary Examiner—Edgar S. Burr
Assistant Examiner—Huong Q. Pham
Attorney, Agent, or Firm—Jerry T. Kearns

[57] ABSTRACT

A scratching device adapted for used by individuals wearing casts consists of an elongated body formed from a flexible material and having two opposed generally rectangular opposing faces. A plurality of spaced obliquely extending linear grooves extend across at least one of the faces. The elongated body may be formed with a hollow interior and provided with a plurality of hollow hemispherical projections on one or both of the faces. Adjacent hemispherical projections face in opposite directions and communicate with the hollow body interior. In use, the device is inserted between the cast and the skin of an individual and linearly reciprocated. The oppositely facing projections collect and remove dead skin cells in the hollow interior. A removable cap adjacent one end of the body allows the interior to be flushed with water for cleaning purposes.

2 Claims, 2 Drawing Sheets

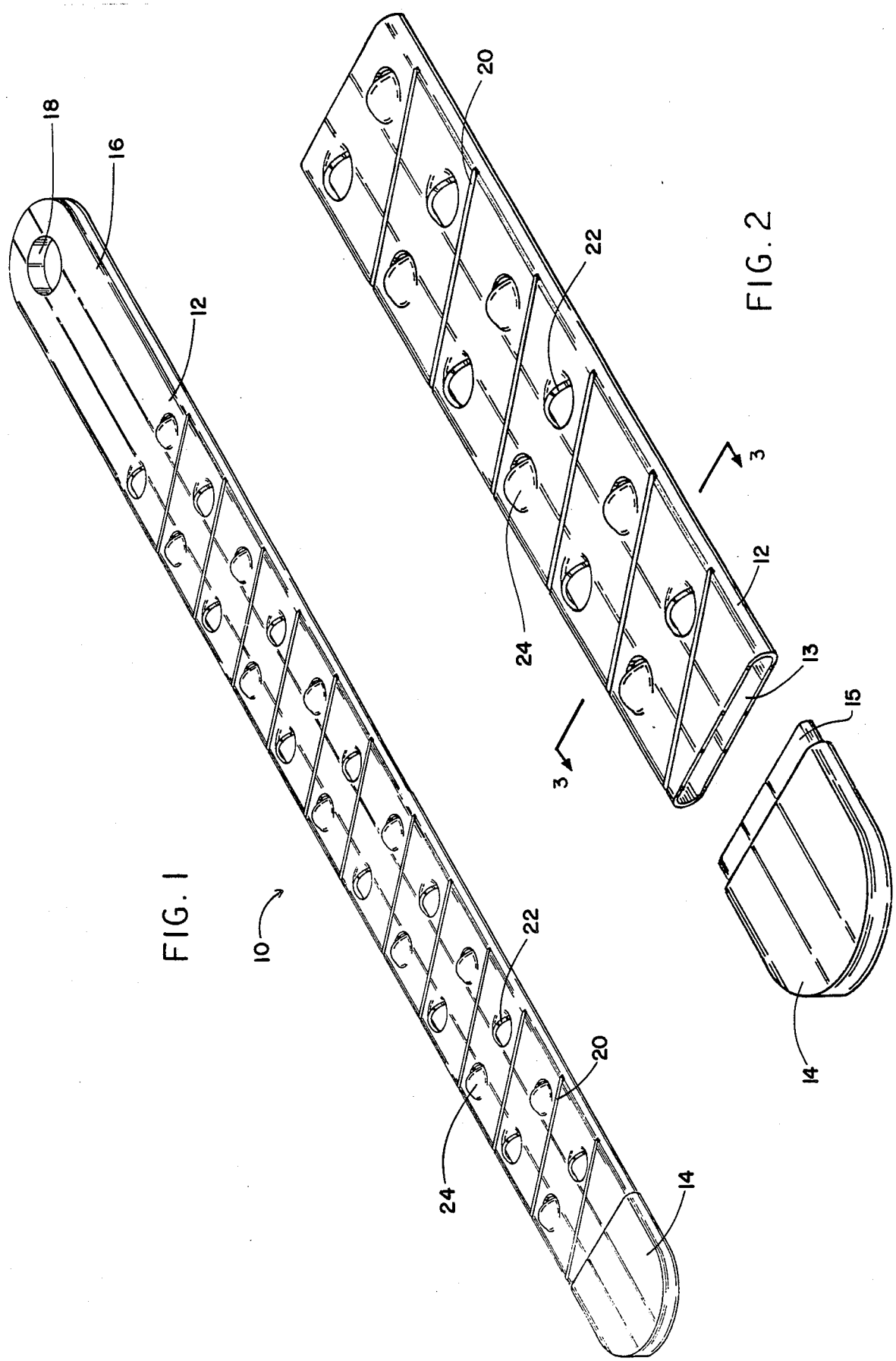

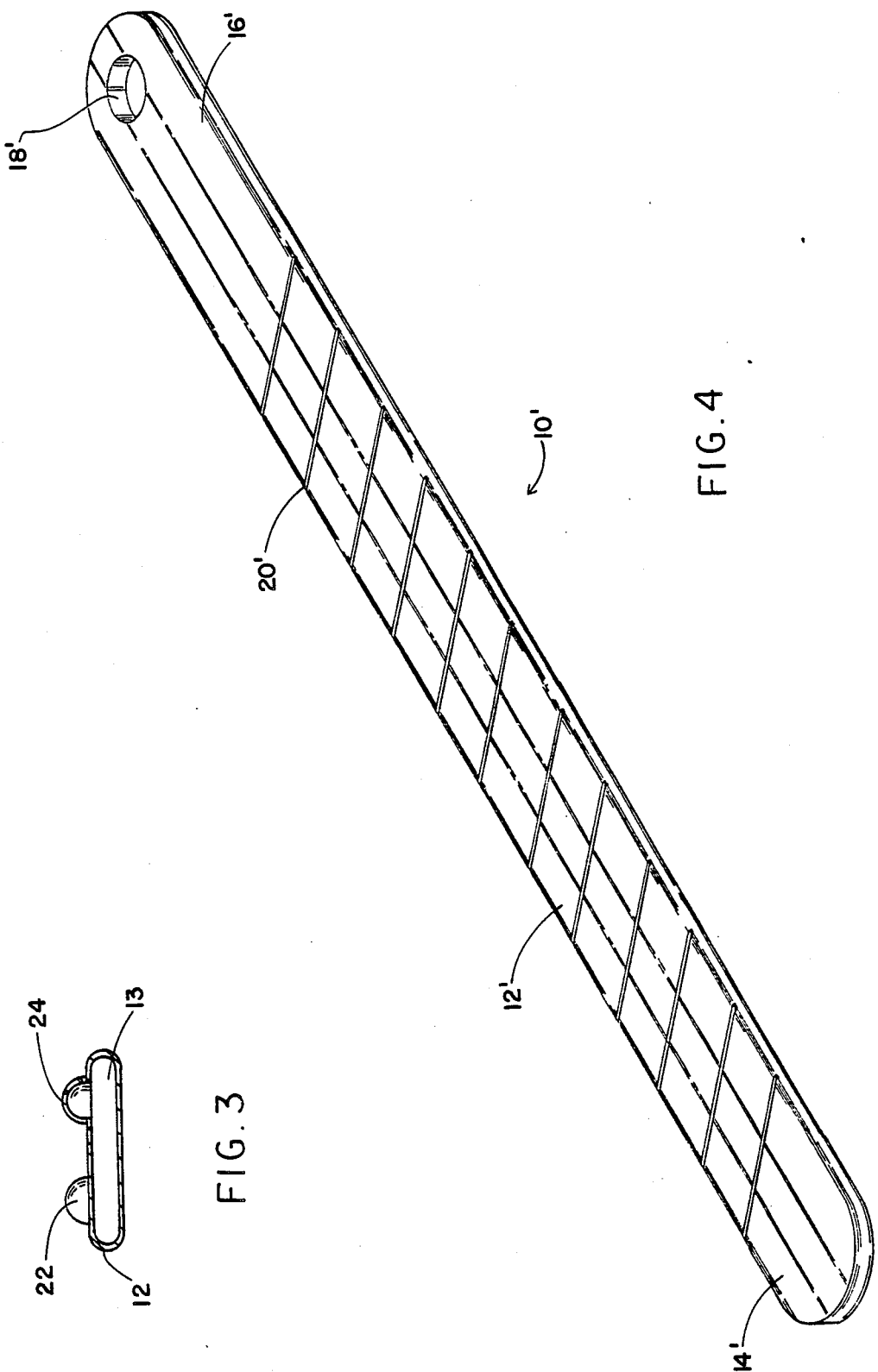

SCRATCHING DEVICE

BACKGROUND OF THE INVENTION

1. Field of the Invention

The present invention relates to scratching devices, and more particularly pertains to a new and improved scratching device specifically adapted for use by individuals wearing casts. Individuals with broken bones and severe sprains frequently have the affected body portion immobilized in a cast. This prevents an individual from washing the casted body portion and also prevents an individual from scratching the body portion enclosed by the cast. Chaffing of the skin area and the preclusion of washing causes a build up of dead skin cells which irritate the individual and causes intense itching. Various types of remedies have been resorted to by such individuals in search of relief. For example, rulers or coat hangers are frequently inserted within the cast and utilized as a scratching implement. These devices provide a temporary relief to the individual, but do not serve to remove the accumulated dead skin cells which cause the skin irritation and resultant itching. In order to overcome this problem, the present invention provides an improved scratching device which removes dead skin cells from a casted area.

2. Description of the Prior Art

Various types of scratching devices are known in the prior art. A typical example of such a scratching device is to be found in U.S. Pat. No. 4,091,491, which issued on May 30, 1978. This patent discloses a cloth mitt, adapted to remove dead dormant skin, which has a raised surface pattern of thread stitching distributed over a substantial area. The rubbing surface may comprise boat sail, canvass or a denim material. U.S. Pat. No. 4,249,521, which issued to J. Gueret on Feb. 10, 1981, discloses a massaging brush including resilient pads having portions which are alternately more flexible when engaged in one direction than when engaged in the opposite direction. Each pad may be discontinuous and take the form of spaced apart fingers or barbs in a row or can be a continuous waving pad. The implement may be formed as a brush, massage glove or soapy water dispensing container. U.S. Pat. No. 4,667,659, which issued to B. Hayday on May 26, 1987, discloses a massaging device for massaging skin within a cast. The device comprises a thin, elongated strip having a plurality of randomly spaced protrusions on one surface and a plurality of rounded indentations in the opposite surface, with the remaining areas of the opposite surface being smooth.

While the above mentioned devices are suited for their intended usage, none of these devices utilize and elongated body formed from a flexible material and provided with a plurality of spaced obliquely extending linear grooves. Additionally, none of the aforesaid devices are formed with a hollow interior and provided with a plurality of alternately oppositely facing hemispherical projections for directing removed dead skin cells to the hollow interior. Inasmuch as the art is relatively crowded with respect to these various types of scratching devices, it can be appreciated that there is a continuing need for and interest in improvements to such scratching devices, and in this respect, the present invention addresses this need and interest.

SUMMARY OF THE INVENTION

In view of the foregoing disadvantages inherent in the known types of scratching devices now present in the prior art, the present invention provides an improved scratching device. As such, the general purpose of the present invention, which will be described subsequently in greater detail, is to provide a new and improved scratching device which has all the advantages of the prior art scratching devices and none of the disadvantages.

To attain this, representative embodiments of the concepts of the present invention are illustrated in the drawings and make use of an elongated body formed from a flexible material and having two opposed generally rectangular opposing faces. A plurality of spaced obliquely extending linear grooves extend across one of the faces. The elongated body may be formed with a hollow interior and provided with a plurality of hollow hemispherical projections on at least one of the faces. The adjacent hemispherical projections face in opposite directions and communicate with the hollow body interior. In use, the device is inserted between the cast and the skin of an individual and linearly reciprocated. The oppositely facing projections collect and remove dead skin cells in the hollow interior. A removable cap adjacent one end of the body allows the interior to be flushed with water for cleaning purposes.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting. As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved scratching device which has all the advantages of the prior art scratching devices and none of the disadvantages.

It is another object of the present invention to provide a new and improved scratching device which may be easily and efficiently manufactured and marketed.

It is a further object of the present invention to provide a new and improved scratching device which is of a durable and reliable construction.

An even further object of the present invention is to provide a new and improved scratching device which is susceptible of a low cost of manufacture with regard to both materials and labor, and which accordingly is then susceptible of low prices of sale to the consuming public, thereby making such scratching devices economically available to the buying public.

Still yet another object of the present invention is to provide a new and improved scratching device which provides in the apparatuses and methods of the prior art some of the advantages thereof, while simultaneously overcoming some of the disadvantages normally associated therewith.

Still another object of the present invention is to provide a new and improved scratching device specifically adapted for use in scratching and removing dead skin cells of body portions enclosed within a cast.

Yet another object of the present invention is to provide a new and improved scratching device which is formed from an elongated flexible body provided with a plurality of spaced obliquely extending linear grooves to remove dead skin cells.

Even still another object of the present invention is to provide a new and improved scratching device which utilizes an elongated flexible body having an hollow interior portion and provided with a plurality of alternately oppositely facing hollow hemispherical projections for removing dead skin cells from a casted body portion.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a perspective view of the scratching device according to a first embodiment of the present invention.

FIG. 2 is an enlarged perspective view of a portion of the scratching device according to the first embodiment of the present invention, with the removable cap removed.

FIG. 3 is a transverse cross sectional view, taken along line 3—3 of FIG. 2.

FIG. 4 is a perspective view illustrating the scratching device according to the second embodiment of the present invention.

DESCRIPTION OF THE PREFERRED EMBODIMENT

With reference now to the drawings, and in particular to FIG. 1 thereof, a new and improVed scratching device embodying the principles and concepts of the present invention and generally designated by the reference numeral 10 will be described.

More specifically, it will be noted that the first embodiment 10 of the invention includes an elongated body 12 preferably formed from a flexible material such as a flexible plastic. The dimensions of the body may be selected depending upon the intended usage, however preferred dimensions are a length of 30 inches, a width of ⅜ inch and a thickness of 1/16 inch. The body 12 has a hollow interior and is provided with a removable cap 14 adjacent one end. A circular aperture 18 is formed through an opposite end 16 of the body 12 for hanging the device on a hook or nail when not in use. A plurality of evenly longitudinally spaced obliquely extending linear grooves 20 extend across the width of at least one face of the body 12. The scratching device has a flat generally rectangular configuration and is provided with radiused end and edge portions to prevent injury to a user. A plurality of hollow hemispherical projections 22 and 24 are spaced along at least one space of the body 12. As illustrated, adjacent pairs of hemispherical projections 22 and 24 face in opposite directions. In use, the body 12 is inserted between the interior cast wall and the skin of an individual and is then linearly reciprocated. The aperture 18 may serve as a finger hole to facilitate this manipulation. The projections 22 and 24 and the grooves 20 serve to alleviate the itching experienced by the individual, as well as to remove the dead skin cells causing this condition. The hollow hemispherical projections 22 and 24 communicate with the hollow interior portion of the body 12 and serve to collect the removed dead skin cells. After use, the cap 14 may be removed to facilitate flushing the interior of the device.

As shown in FIG. 2, the cap 14 has a stepped flange 15 dimensioned for frictional engagement within the hollow interior 13 of the body 12.

FIG. 3 provides a transverse cross sectional view illustrating the oppositely facing projections 22 and 24 communicating with the hollow interior 13. While the oblique linear grooves 20 and projections 22 and 24 have been illustrated and described with reference to only one of the rectangular faces of the body 12, it is to be understood that both the projections 22 and 24 in the grooves 20 may be provided in similar fashion on both opposed rectangular faces without departing from the scope of the present invention.

FIG. 4 illustrates a second embodiment 10' of the invention in which the elongated body 12' is formed from a solid thin flexible strip of a plastic material and is provided with a plurality of longitudinally spaced oblique grooves 20'. The grooves 20' may be provided on both opposed faces of the device 10'. The radiused end 14' is integrally formed with the body 12' and a second integrally formed end 16' is also radiused and is provided with an aperture 18' to provide a finger loop to facilitate manipulation of the device as well as to allow storage of the device when not in use. The scratching device 10' of the second embodiment of the present invention is not provided with raised hemispherical projections and does not have a hollow interior portion. Nevertheless, the flexible nature of the body 12' in conjunction with the obliquely extending grooves 20' allows the device to be easily inserted and linearly reciprocated to remove dead skin cells and provide relief from irritation.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by letters patent of the United States is as follows:

1. A scratching device, comprising:
    an elongated body having two opposed generally flat rectangular faces, said body formed from a flexible material and having a hollow internal portion;
    an open end at one end of said body communicating with said hollow interior portion;
    a removable cap on said open end of said body;
    a plurality of linear grooves spaced along the length of at least one of said faces of said body, said grooves each extending at an oblique angle with respect to a longitudinal axis of said body; and
    a plurality of hollow hemispherical projections on at least one of said faces, said hemispherical projections each having an arcuate scraping edge and each communicating with said hollow interior portion.
2. The scratching device of claim 1, wherein adjacent hemispherical projections face in opposite directions.

* * * * *